US007901386B2

(12) United States Patent
Hishikawa et al.

(10) Patent No.: US 7,901,386 B2
(45) Date of Patent: Mar. 8, 2011

(54) LIQUID TRANSFUSING TUBE AND LIQUID TRANSFUSING TUBE SET

(75) Inventors: Yoshinori Hishikawa, Yamanashi (JP); Takayuki Yokota, Yamanashi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1250 days.

(21) Appl. No.: 10/534,364

(22) PCT Filed: Oct. 16, 2003

(86) PCT No.: PCT/JP03/13223
§ 371 (c)(1), (2), (4) Date: May 9, 2005

(87) PCT Pub. No.: WO2004/047887
PCT Pub. Date: Jun. 10, 2004

(65) Prior Publication Data
US 2006/0155249 A1    Jul. 13, 2006

(30) Foreign Application Priority Data

Nov. 26, 2002    (JP) .................................. 2002-342442

(51) Int. Cl.
*A61M 5/00*    (2006.01)
(52) U.S. Cl. ..................................... 604/258; 604/93.01
(58) Field of Classification Search .................... 604/30, 604/38, 251–259, 122, 93.01; 137/883
See application file for complete search history.

(56) References Cited

U.S. PATENT DOCUMENTS

| 4,447,230 A | * | 5/1984 | Gula et al. | 604/122 |
| 4,734,091 A | * | 3/1988 | Boyle et al. | 604/521 |
| 4,941,875 A |   | 7/1990 | Brennan |   |

FOREIGN PATENT DOCUMENTS

| CA | 1012431 | 6/1977 |
| EP | 1 043 038 A2 | 10/2000 |
| EP | 1 129 682 A2 | 9/2001 |
| EP | 1 129 682 A3 | 9/2001 |
| EP | 1 221 320 A2 | 7/2002 |
| JP | 4-354952 A | 12/1992 |
| WO | WO 99/34846 A2 | 7/1999 |
| WO | WO 99/34846 A3 | 7/1999 |

OTHER PUBLICATIONS

Supplementary European Search Report issued in EP 03 75 6631.2, Nov. 6, 2008, European Patent Office, Munich, DE.

* cited by examiner

*Primary Examiner* — Nicholas D Lucchesi
*Assistant Examiner* — Brooke M Matney
(74) *Attorney, Agent, or Firm* — Buchanan Ingersoll & Rooney PC

(57) ABSTRACT

A liquid transfusing tube and a liquid transfusing tube set in which a liquid transfusing line can be extended readily and quickly. The liquid transfusing tube comprises a flexible tube constituting the liquid transfusing channel, a connector provided at one end part of the tube, and a pointed bottle needle provided at the other end part of the tube and being connected to the side of a liquid transfusing bag containing a liquid being transfused. A roller klemme and a drip tube are provided in the middle of the tube. The connector has two female connectors, a male connector, and an operating lever and the communication pattern between the inner cavity of the female connector and that of the female connector or that of the male connector can be selected by means of the operating lever.

10 Claims, 9 Drawing Sheets

LIQUID TRANSFUSING TUBE AND LIQUID TRANSFUSING TUBE SET

TECHNICAL FIELD

The present invention relates to a liquid transfusing tube and a liquid transfusing tube set.

BACKGROUND ART

In a conventional liquid transfusing set (liquid transfusing apparatus), a liquid transfusing tube is provided with a male lure connector at its end part (distal end) on the side of connection to a patient. Therefore, in order to secure a plurality of liquid transfusing routes, it has been necessary to provide the tube on the patient's side with a three-way cock, a multiple-way cock, or the like so as to obtain the condition in which a liquid transfusing route or routes can be additionally provided, i.e., the plurality of liquid transfusing tubes can be connected (see, for example, Japanese Patent Laid-open No. Hei 4-354952).

For example, although liquid transfusing sets having a three-way cock provided at an intermediate part of a liquid transfusing route have been commercialized, the number of liquid transfusing routes required varies depending on the patient or the patient's condition, and the number of liquid transfusing routes, which must preliminarily be prepared, is not known. In view of this, it is a general practice to collect data on the number of liquid transfusing routes used from many patients, calculate an average number of liquid transfusing routes used from the data, and configure the liquid transfusing routes by providing reserve ports capable of connection with liquid transfusing tubes the number, which number is one or two greater than the average number of liquid transfusing tubes used.

However, the patients requiring the reserve ports are in many cases those whose conditions are highly liable to change suddenly, and most of the patients to be treated by the liquid transfusing treatment do not require the reserve ports. However, the liquid transfusing sets provided with the reserve ports must be prepared for the small number of patients, which raises the cost of the liquid transfusing sets, or increases the number of kinds of the liquid transfusing sets to be prepared in each hospital, which costs much for stock control, leading to a rise in medical expense.

In addition, when the number of kinds of liquid transfusing sets has been increased, it is necessary to selectively use the different kinds of liquid transfusing sets, leading to a higher risk of making a mistake in the method of using the same.

Moreover, when the patient's condition has changed suddenly or in other similar situations, the reserve ports prepared beforehand may temporarily become insufficient.

In such a case, it is necessary to once stop the liquid transfusion, occlude the liquid transfusing route, then open the liquid transfusing route, and to assemble a three-way cock or the like into the course of the liquid transfusing route. In this instance, it is necessary to carry out a work needing much labor and time, i.e., to assemble the cock into the liquid transfusing route, apply syringe suction for removing air, which has been mixed into the liquid transfusing route on the patient's side, perform priming of the liquid on the stopped side, thereby eliminating air stagnating in the liquid transfusing route, and then to connect the liquid transfusing tube.

Besides, the liquid transfusing routes may be mis-connected, or dosing speed may be mis-set in again setting the flow rate (setting the dosing speed).

In addition, when suction through a syringe is applied to removal of air present in the liquid transfusing route on the patient's side, the patient's blood may flow back into a catheter indwelling in the patient, and the blood may become liable to coagulate, possibly causing the formation of thrombus. Therefore, it becomes necessary to exchange the indwelling catheter earlier than scheduled, which adversely affects the patient.

Besides, although there are needleless connectors developed for preventing puncture accidents in medical staff or for maintaining cleanliness at the time of connection, the needleless connectors are based on the assumption of closed circuits. Therefore, it is impossible to increase the number of liquid transfusing tube connection locations in the course of the liquid transfusing route. In the situation where the number of the connection locations is insufficient, it is necessary to adopt a use method in which the portion on the distal end of the liquid transfusing route provided with the needleless connector is opened and which considerably impairs the characteristic feature of connecting the liquid fusing tubes while maintaining the cleanliness in a closed circuit. Also in this case, like in the above-mentioned case, the method in which a larger number of reserve ports than expected to be needed are provided results in that it is unknown how many reserve ports should be provided. Eventually, the number of reserve ports will be insufficient. In this manner, the rise in cost, the labor and time taken for air removal, the risk of generating a mistake in setting the dosing speed, and a cause of thrombus, are the same as in the above-mentioned case.

DISCLOSURE OF INVENTION

In order to solve the above-mentioned problems involved in the related art, the present invention has an object of providing a liquid transfusing tube and a liquid transfusing tube set in which a liquid transfusing line (liquid transfusing route) can be extended readily and quickly.

The above object can be attained by the present invention as set forth in the following paragraphs (1) to (17).

(1) A liquid transfusing tube including:
a tube constituting a liquid transfusing channel;
a connector provided at one end part of the tube and having a male connector and a female connector; and
a connection part provided on the other side of the tube and connected to the side of a containing part containing the liquid being transfused.

(2) A liquid transfusing tube as set forth in the above paragraph (1), wherein the axis of the male connector and the axis of the female connector substantially coincide with each other.

(3) The liquid transfusing tube as set forth in the above paragraph (1) or (2), wherein the connector has a channel changeover function for changing over the channel.

(4) The liquid transfusing tube as set forth in the above paragraph (1) or (2), wherein the connector is so configured as to be capable of selecting a communication pattern between the inner cavity of the tube, the inner cavity of the male connector, and the inner cavity of the female connector.

(5) The liquid transfusing tube as set forth in any of the above paragraphs (1) to (4), wherein the connection part is a bottle needle connected to a liquid container.

(6) The liquid transfusing tube as set forth in any of the above paragraphs (1) to (4), wherein the connection part is connected to a syringe.

(7) The liquid transfusing tube as set forth in any of the above paragraphs (1) to (6), including flow rate regulating means for regulating the flow rate of the transfusion, in the course of the tube.

(8) The liquid transfusing tube as set forth in any of the above paragraphs (1) to (7), including reverse flow inhibitive means for permitting a flow from the connection part to the connector while inhibiting a flow in the reverse direction, in the course of the tube.

(9) The liquid transfusing tube as set forth in any of the above paragraphs (1) to (8), wherein the male connector of the connector is so shaped as to be capable of liquid-tight connection to another female connector having the same shape as that of the above-mentioned female connector.

(10) The liquid transfusing tube as set forth in any of the above paragraphs (1) to (9), wherein the female connector of the connector is so shaped as to be capable of liquid-tight connection to another male connector having the same shape as that of the above-mentioned male connector.

(11) A liquid transfusing tube set including:
at least one liquid transfusing tube as set forth in any of the above paragraphs (1) to (10); and
a liquid dosing part for dosing a patient with the liquid being transfused, the liquid dosing part having a liquid dosing part side connector capable of being connected to the male connector or the female connector of the connector of the liquid transfusing tube.

(12) The liquid transfusing tube set as set forth in the above paragraph (11), wherein the liquid dosing part has a bacteria-removing filter.

(13) The liquid transfusing tube set as set forth in the above paragraph (12), wherein the bacteria-removing filter is provided on the downstream side relative to the liquid dosing part side connector.

(14) The liquid transfusing tube set as set forth in the above paragraph (12) or (13), wherein the liquid dosing part has a mixing injection port on the downstream side of the bacteria-removing filter.

(15) The liquid transfusing tube set as set forth in the above paragraph (14), wherein the mixing injection port can be connected to the male connector or the female connector of the connector of the liquid transfusing tube.

(16) The liquid transfusing tube set as set forth in any of the above paragraphs (11) to (15), wherein the other end side of a tube having on its one end side a connection part connected to a liquid container is connected to the liquid dosing part side connector.

(17) The liquid transfusing tube set as set forth in any of the above paragraphs (11) to (15), wherein the liquid dosing part side connector is branched into a plurality of parts so that a connector provided on the other end side of a tube having on its one end side a connection part connected to another liquid container other than the liquid container and the connector of the liquid transfusing tube can be simultaneously connected.

BEST MODE FOR CARRYING OUT THE INVENTION

Now, the liquid transfusing tube and the liquid transfusing tube set according to the present invention will be described in detail below, based on preferred embodiments shown in the accompanying drawings.

Figure 1:
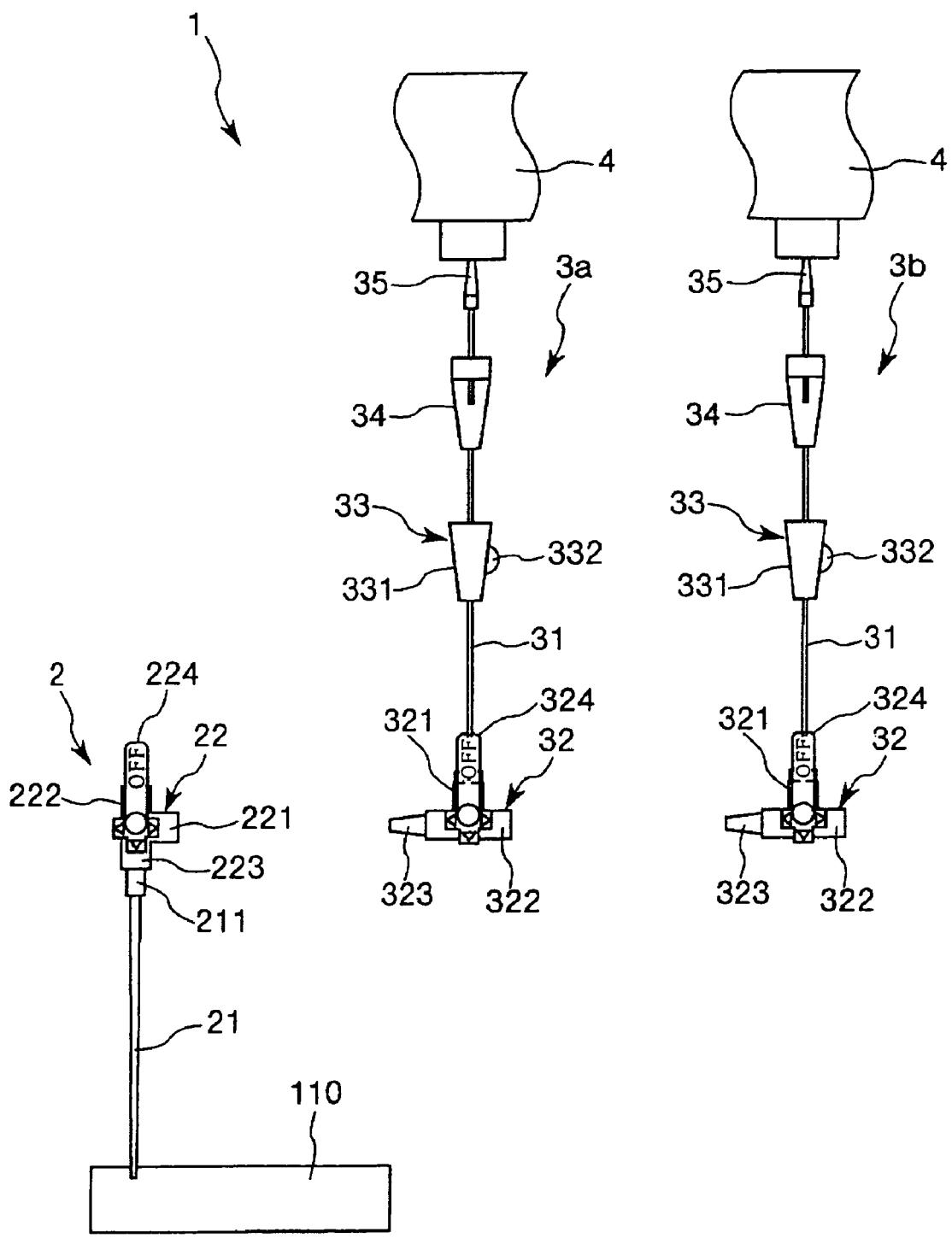
FIG. 1 is a plan view showing a first embodiment of a liquid transfusing tube set according to the present invention.
Figure 2:
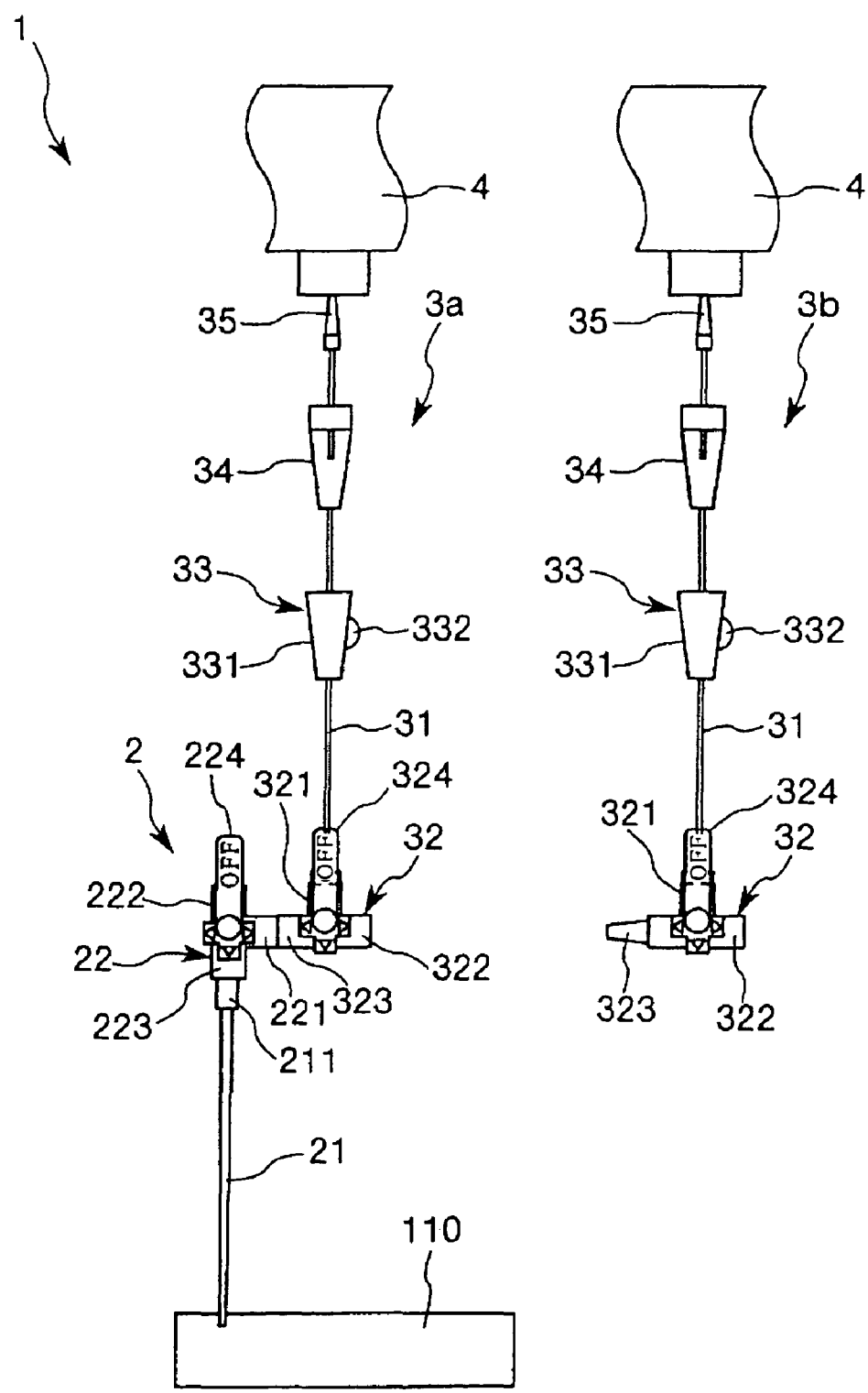
FIG. 2 is a plan view showing the condition where one of liquid transfusing tubes of the liquid transfusing tube set shown in FIG. 1 is connected.
Figure 3:
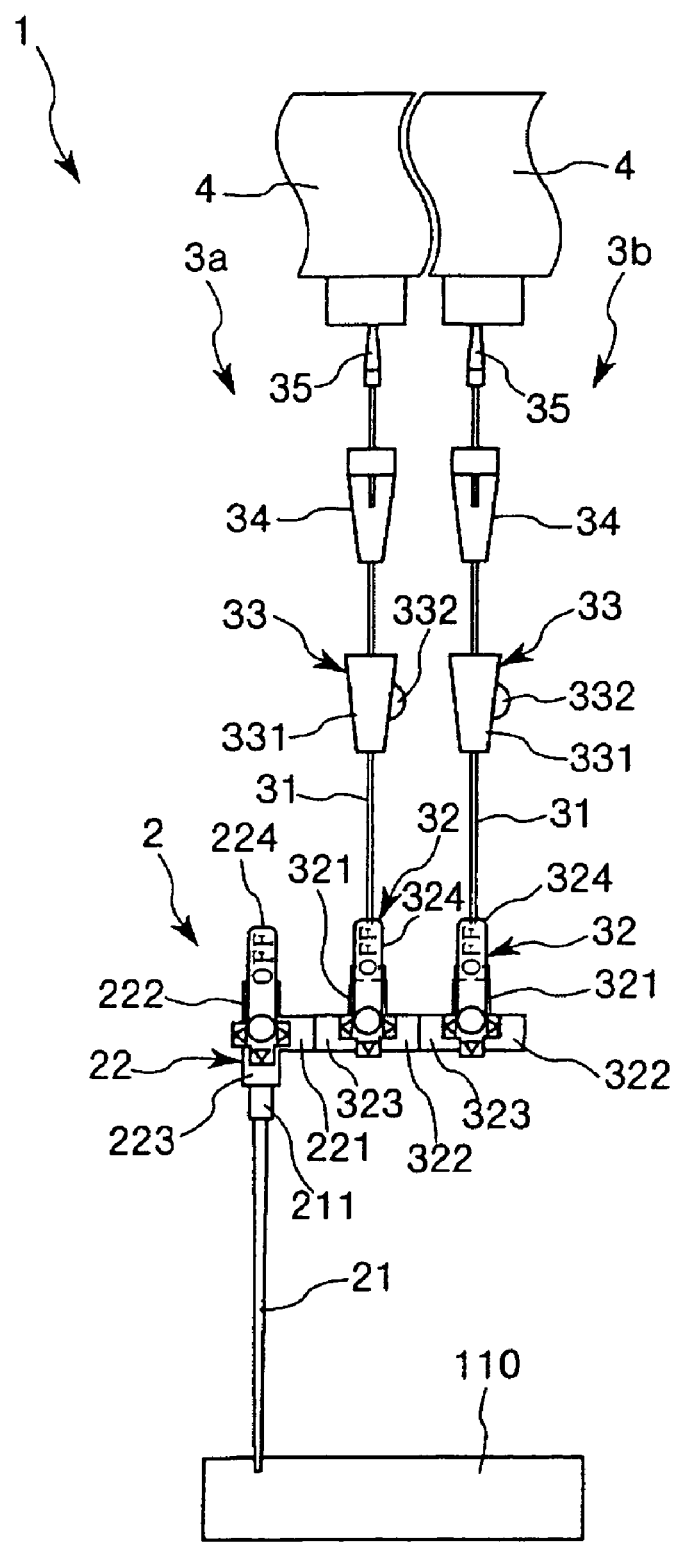
FIG. 3 is a plan view showing the condition where each of the liquid transfusing tubes of the liquid transfusing tube set shown in FIG. 1 is connected.

FIG. 1 is a plan view showing a first embodiment of the liquid transfusing tube set according to the present invention, FIG. 2 is a plan view showing the condition where one of liquid transfusing tubes of the liquid transfusing tube set shown in FIG. 1 is connected, and FIG. 3 is a plan view showing the condition where each of the liquid transfusing tubes of the liquid transfusing tube set shown in FIG. 1 is connected.

Incidentally, for convenience of description, in FIGS. 1 to 3, the side of the blood vessel of the patient in the figures will be referred to as "the distal end", and the side of the blood bag will be referred to as "the proximal end".

The liquid transfusing tube set (liquid transfusing set) 1 shown in these figures is an apparatus (set) for injecting (dosing) a liquid (transfusion) into a living body (patient).

The transfusion includes all the liquids, which can be dosed into the living body, such as chemical liquids, correction electrolyte liquids, physiological saline, etc.

In addition, the kind of the chemical in the chemical liquid is not particularly limited, and examples of the chemical include sedative, intravenous anesthetic, narcotic analgesic, local anesthetic, antidepolarizing muscle relaxant, vasopressor, hypotensive agent, coronary vasodilator, diuretic, antiarrhythmic agent, bronchodilator, hemostatic, vitamin agent, antibiotic drug, and lipid emulsion.

As shown in FIG. 1, the liquid transfusing tube set 1 has a liquid dosing part 2 for dosing a patient with the transfusion, and a plurality of liquid transfusing tubes (in this embodiment, two liquid transfusing tubes 3a and 3b) which can be connected to the liquid dosing part through a connector. These components will be sequentially described below.

The liquid dosing part 2 has an indwelling needle or catheter (in this embodiment, an indwelling needle 21) permitted to indwell in a blood vessel 110 of the patient, and a liquid dosing part side connector 22 connected to a proximal end of the indwelling needle or catheter (in this embodiment, the indwelling needle 21).

The material constituting the indwelling needle 21 is preferably a flexible polymer material, and examples thereof include thermoplastic resins such as polyolefins such as polyethylene, polypropylene, etc., polyesters, and polyurethanes.

Incidentally, a tube not shown may be provided between the indwelling needle 21 (or catheter) and the liquid dosing part side connector 22 so as to connect the indwelling needle 21 (or catheter) and the liquid dosing part side connector 22 to each other through the tube. In this case, the liquid dosing part side connector 22 may be provided at an end part of the tube, or may be provided in the course of the tube.

The liquid dosing part side connector 22 is not particularly limited inasmuch as it has a female connector or a male connector connectable to a male connector 323 or a female connector 322 of a connector 32 of liquid transfusing tubes 3a, 3b, which will be described later. In this embodiment, a three-way cock is used as the liquid dosing part side connector 22.

The liquid dosing part side connector 22 has two female connectors 221, 222, a male connector 223, and an operating lever (operating part) 224, and is so configured that a communication pattern between the inner cavity of the female connector 221, the inner cavity of the female connector 222, and the inner cavity of the male connector 223 can be selected by the operating lever 224 (the liquid dosing part side connector 22 has a channel changeover function for changing over the channel).

Specifically, the liquid dosing part side connector 22 is so configured that the operating lever 224 can be moved to each of four positions, i.e., the position of the female connector 221, the position of the female connector 222, the position of the male connector 223, and a position where no connector is present (in FIG. 1, the position where the operating lever 224 is directed in the sense opposite to the male connector 221). When the operating lever is moved to the position of the female connector 221, the inner cavity of the female connector 222 and the inner cavity of the male connector 223 are communicated with each other. When the operating lever 224 is moved to the position of the female connector 222, the inner cavity of the female connector 221 and the inner cavity of the male connector 223 are communicated with each other. When the operating lever 224 is moved to the position of the male connector 223, the inner cavity of the female connector 221 and the inner cavity of the female connector 222 are communicated with each other. When the operating lever 224 is moved to the position where no connector is present, the inner cavity of the female connector 221, the inner cavity of the female connector 222, and the inner cavity of the male connector 223 are all communicated with one another.

In addition, the axis of the male connector 223 and the axis of the female connector 222 coincide substantially with each other, and the axis of the female connector 221 is substantially orthogonal to these axes. The male connector 223 and the female connector 222 are substantially coaxial with each other and are directed in opposite senses, whereas the female connector 221 is set in a direction substantially orthogonal to the male connector 223 and the female connector 222.

Besides, the female connectors 221 and 222 are so shaped as to be capable of liquid-tight connection with a male connector 323 of a connector 32 of a liquid transfusing tubes 3a or 3b, which will be described later.

Incidentally, while the male connector 323 of the connector 32 of the liquid transfusing tube 3a or 3b is connected to the liquid dosing part side connector 22 in this embodiment, a female connector 322 of the connector 32 of the liquid transfusing tube 3a or 3b may be connected to the liquid dosing part side connector 22. Alternatively, both the male connector 323 and the female connector 322 of the connector 32 of the liquid transfusing tube 3a or 3b may be capable of connection to the liquid dosing part side connector 22.

In the case where the male connector 322 of the connector 32 of the liquid transfusing tube 3a or 3b is connected to the liquid dosing part side connector 22, for example, the female connectors 221 and 222 of the liquid dosing part side connector 22 are replaced by male connectors, which are so shaped as to be capable of liquid-tight connection with the female connector 322 of the connector 32 of the liquid transfusing tube 3a or 3b.

Besides, in the case where both the male connector 323 and the female connector 322 of the connector 32 of the liquid transfusing tube 3a or 3b can be connected to the liquid dosing part side connector 22, for example, one of the male connectors 221 and 222 of the liquid dosing part side connector 22 is replaced by a male connector, which is so shaped as to be capable of liquid-tight connection to the female connector 322 of the connector 32 of the liquid transfusing tube 3a or 3b.

The indwelling needle 21 has an outlet port 211 at its proximal end. The male connector 223 of the liquid dosing part side connector 22 is in liquid-tight connection with the outlet port 211.

Now, the liquid transfusing tubes 3a and 3b will be described below. Since the liquid transfusing tube 3a and the liquid transfusing tube 3b are configured in the same manner, one of them, i.e., the liquid transfusing tube 3a will be described as a representative of them.

The liquid transfusing tube 3a includes a tube 31, a connector (branch tube) 32, and a bottle needle 35. The tube 31 is flexible and constitutes the liquid transfusing channel. The connector (branch tube) 32 is provided at one end part (distal end) of the tube 31 and has a male connector and a female connector. The bottle needle 35 has a sharp needle tip and is provided on the other side (in this embodiment, at the other end part [proximal end]) of the tube 31 so as to function as a connection part to be connected to the side of a liquid transfusing bag (liquid transfusing container) (containing part) 4 containing the liquid being transfused.

In addition, at an intermediate part of the tube 31, a roller klemme (roller type klemme) 33 and a drip tube 34 are provided as flow rate regulating means for regulating the flow rate of the transfusion.

A predetermined transfusion is contained in the liquid transfusing bag 4. When the bottle needle 35 pierces (punctures) a plug (rubber plug) of the liquid transfusing bag 4, the liquid transfusing bag 4 and the liquid transfusing tube 3a are connected to each other through the bottle needle 35, resulting in the condition where the transfusion can be supplied from the liquid transfusing bag 4 to the side of the liquid transfusing tube 3a.

The drip tube 34 is disposed in the vicinity of the bottle needle 35. The drip tube 34 makes it possible to visually check the flow rate of the transfusion.

The roller klemme 33 is disposed between the connector 32 and the drip tube 34.

The roller klemme 33 is composed of a klemme main body 331, and a roller (operating part) 332 disposed to be movable relative to the klemme main body 331. The tube 31 is clamped between the outer peripheral surface of the roller 332 and a bottom surface (inclined surface) inclined at a predetermined angle against the klemme main body 331, and the roller 332 is moved relative to the klemme main body 331, whereby the degree of clamping the tube 31 is varied, and the flow rate of the transfusion is thereby regulated.

With the roller 332 moved in a predetermined direction, the degree of clamping the tube 31 is enhanced, and the flow rate of the transfusion is reduced. When the roller 332 is moved to the utmost, the inner cavity of the tube 31 is occluded, so that the liquid being transfused will not flow.

On the other hand, with the roller 332 moved in the sense reverse to the above, the degree of clamping the tube 31 is reduced, and the flow rate of the transfusion is increased.

When the roller 332 is moved to the utmost in this sense, the inner cavity of the tube 31 is fully opened, so that the flow rate of the transfusion is maximized.

The connector 32 is not particularly limited inasmuch as it includes a male connector and a female connector; in this embodiment, a three-way cock is used as the connector 32.

The connector 32 includes two female connectors 321, 322, a male connector 323, and an operating lever (operating part) 324, and the communication pattern among the inner cavity of the female connector 321, the inner cavity of the female connector 322, and the inner cavity of the male connector 323 can be selectively obtained by means of the operating lever 324 (thus, the connector 32 has a channel changeover function for changing over the channel).

Specifically, the connector 32 is so configured that the operating lever 324 can be moved to the four positions, i.e., the position of the female connector 321, the position of the female connector 322, the position of the male connector 323, and the position where no connector is present (the position where the operating lever 324 is set in the sense opposite to the female connector 321 in FIG. 1). When the operating lever 324 is moved to the position of the female connector 321, the inner cavity of the female connector 322 and the inner cavity of the male connector 323 are communicated with each other. When the operating lever 324 is moved to the position of the female connector 322, the inner cavity of the female connector 321 and the inner cavity of the male connector 323 are communicated with each other. When the operating lever 324 is moved to the position of the male connector 323, the inner cavity of the female connector 321 and the inner cavity of the female connector 322 are communicated with each other. When the operating lever 324 is moved to the position where no connector is present, the inner cavity of the female connector 321, the inner cavity of the female connector 322, and the inner cavity of the male connector 323 are all communicated one another.

In addition, the axis of the male connector 323 and the axis of the female connector 322 substantially coincide with each other, and the axis of the female connector 321 is substantially orthogonal to these axes. In other words, the male connector 323 and the female connector 322 are substantially coaxial with each other and are directed in opposite senses, and the female connector 321 is set in a direction substantially perpendicular to the male connector 323 and the female connector 322.

The tube 31 is provided at its distal end with a male connector, which is not shown, and the male connector is in liquid-tight connection to the female connector 321 of the connector 32. Incidentally, the distal end of the tube 31 may be joined directly to the female connector 321.

Here, the male connector 323 of the connector 32 is so shaped as to be capable of liquid-tight connection with another female connector having the same shape as that of the female connector 322.

This ensures that the male connector 323 of the connector 32 of the liquid transfusing tube 3a can be connected in a liquid-tight manner to a female connector of a connector of another liquid transfusing tube (for example, the female connector 322 of the connector 32 of the liquid transfusing tube 3b).

Besides, the female connector 322 of the connector 32 is so shaped as to be capable of liquid-tight connection to another male connector having the same shape as that of the male connector 323.

This ensures that a male connector of a connector of another liquid transfusing tube (for example, the male connector 323 of the connector 32 of the liquid transfusing tube 3b) can be connected in a liquid-tight manner to the female connector 322 of the connector 32 of the liquid transfusing tube 3a.

In this manner, the connector 32 of any liquid transfusing tube can be connected to the connector 32 of another liquid transfusing tube (any number of connectors 32 can be connected). For example, it is possible to connect the connector 32 of the liquid transfusing tube 3b to the connector 32 of the liquid transfusing tube 3a, to connect the connector 32 of another liquid transfusing tube not shown to the connector 32 of the liquid transfusing tube 3b, and thereafter to sequentially connect the connectors 32 of other liquid transfusing tubes in a similar manner.

Incidentally, while the connector 32 is the three-way cock in this embodiment, in the present invention the connector 32 is not limited to the three-way cock inasmuch as it is a connector having a male connector and a female connector; for example, a connector not having the function of changing over the channel, such as a needleless connector having a male connector and a female connector, may be adopted as the connector 32.

The material constituting the tube 31 may be any of a wide range of materials conventionally used for medical tubes, and specific examples of the material include soft polyvinyl chloride, ethylene-vinyl acetate copolymer, polybutadiene, etc., and materials based on these polymers.

Now, the actions of (method of using) the liquid transfusing tube set 1 will be described below.

Here, description will be made taking as an example the case where the liquid transfusing tube 3a is used as a first liquid transfusing line (first liquid transfusing route) for dosing a transfusion into a patient, i.e., principally as a liquid transfusing tube for flow therethrough of a fundamental liquid or the like, and the liquid transfusing tube 3b is used as a second liquid transfusing line (second liquid transfusing route) for dosing a transfusion into the patient, i.e., principally as an auxiliary route, for example, a liquid transfusing tube for flow therethrough of a lipid emulsion, a remedy, an antibiotic drug, or the like.

In connecting the liquid transfusing tube 3a, first, a retentive liquid agent, for example, is prepared in the liquid transfusing bag 4.

Next, as shown in FIG. 1, the bottle needle 35 of the liquid transfusing tube 3a is made to pierce (puncture) a plug (rubber plug) of the liquid transfusing bag 4 in which the transfusion is contained. This ensures that the liquid transfusing bag 4 and the liquid transfusing tube 3a are connected to each other through the bottle needle 35, resulting in the condition where the transfusion can be supplied from the liquid transfusing bag 4 to the side of the liquid transfusing tube 3a.

Subsequently, priming of the channel of the liquid transfusing tube 3a is performed.

Next, as shown in FIG. 2, the male connector 323 of the connector 32 of the liquid transfusing tube 3a is inserted and fitted into the female connector 221 of the liquid dosing part side connector 22 having its female connector 223 in liquid-tight connection with the outlet port 211 of the indwelling needle 21 left indwelling in a blood vessel (for example, a peripheral vein) 110 of the patient. This results in that the female connector 221 of the liquid dosing part side connector 22 and the male connector 323 of the connector 32 of the liquid transfusing tube 3a are connected liquid-tight with each other.

Subsequently, the operating lever 224 of the liquid dosing part side connector 22 is moved to the position of the female connector 222, and the operating lever 324 of the connector 32 of the liquid transfusing tube 3a is moved to the position of the female connector 322. This results in that the inner cavity of the female connector 221 and the inner cavity of the male connector 223 of the liquid dosing part side connector 22 are communicated with each other, and the inner cavity of the female connector 321 and the inner cavity of the male connector 323 of the connector 32 of the liquid transfusing tube 3a are communicated with each other.

Next, the roller klemme 33 of the liquid transfusing tube 3a is operated to regulate the flow rate (dose rate) of the transfusion in the liquid transfusing tube 3a to a prescribed flow rate (prescribed dose rate) of the retentive liquid agent, and the transfusion is dosed.

Incidentally, the male connector 323 of the connector 32 of the liquid transfusing tube 3a may be connected to the female connector 222 of the liquid dosing part side connector 22. In this case, the operating lever 224 of the liquid dosing part side connector 22 is moved to the position of the female connector 221, thereby achieving communication between the inner cavity of the female connector 222 and the inner cavity of the male connector 223 of the liquid dosing part side connector 22.

In addition, the liquid dosing part side connector 22 may be omitted, and the male connector 323 of the connector 32 of the liquid transfusing tube 3a may be connected to the outlet port 211 of the indwelling needle 21. In this case, the male connector 323 and the outlet port 211 are shaped for liquid-tight connection with each other.

Next, in connecting the liquid transfusing tube 3b used for dosing an antibiotic drug, for example, at regular time intervals depending on the condition of the patient, first, physiological saline containing the antibiotic drug dissolved therein is prepared in the liquid transfusing bag 4.

Subsequently, as shown in FIG. 2, the bottle needle 35 of the liquid transfusing tube 3b is made to pierce (puncture) a plug (rubber plug) of the liquid transfusing bag 4 in which the transfusion is contained. This ensures that the liquid transfusing bag 4 and the liquid transfusing tube 3b are connected to each other through the bottle needle 35, resulting in the condition where the transfusion can be supplied from the liquid transfusing bag 4 to the side of the liquid transfusing tube 3b.

Next, priming of the channel of the liquid transfusing tube 3b is conducted.

Subsequently, as shown in FIG. 3, the male connector 323 of the connector 32 of the liquid transfusing tube 3b is inserted and fitted into the female connector 322 of the connector 32 of the liquid transfusing tube 3a. This results in liquid-tight connection between the female connector 322 of the connector 32 of the liquid transfusing tube 3a and the male connector 323 of the connector 32 of the liquid transfusing tube 3b.

Next, the operating lever 324 of the connector 32 of the liquid transfusing tube 3b is moved to the position of the female connector 322. This makes communication between the inner cavity of the female connector 321 and the inner cavity of the male connector 323, of the connector 32 of the liquid transfusing tube 3b.

Subsequently, the operating lever 324 of the connector 32 of the liquid transfusing tube 3a is moved to the position where no connector is present (the position where the operating lever 324 is set in the sense opposite to the female connector 321 in FIG. 3). This results in that the inner cavity of the female connector 321, the inner cavity of the female connector 322, and the inner cavity of the male connector 323, of the connector 32 of the liquid transfusing tube 3a, are all communicated with one another.

Next, the roller klemme 33 of the liquid transfusing tube 3b is operated to regulate the flow rate (dose rate) of the transfusion in the liquid transfusing tube 3b to a designated flow rate (designated dose rate) of an antibiotic drug, and the transfusion is dosed.

In this manner, the patient can be dosed (mixedly dosed) with the retentive liquid agent via the liquid transfusing tube 3a and with the physiological saline containing the antibiotic drug dissolved therein via the liquid transfusing tube 3b.

In addition, where the liquid transfusing line (liquid transfusing route) is extended, the male connector 323 of the connector 32 of an other liquid transfusing tube not shown is inserted and fitted into the female connector 322 of the connector 32 of the liquid transfusing tube 3b, in the same manner as above. This results in liquid-tight connection between the female connector 322 of the connector 32 of the liquid transfusing tube 3b and the male connector 323 of the connector 32 of the other liquid transfusing tube.

Thereafter, any number of liquid transfusing lines can be extended in the same manner.

Incidentally, the above-described method of using the liquid transfusing tube set 1 is merely one example, which is nonlimitative.

For example, in the case where a patient is dosed with a transfusion via the liquid transfusing tube 3a, the liquid may be replenished via the liquid transfusing tube 3b.

As has been described above, according to the liquid transfusing tube set 1, a port (female connector 322) for connection of a liquid transfusing tube is always present, so that the liquid transfusing line (liquid transfusing route) can be extended quickly and assuredly.

Since the port (female connector 322) for connection of a liquid transfusing tube is always present, there is no possibility of the condition where, for example, the number of the connection ports for liquid transfusing tubes would be insufficient upon a sudden change in the condition of the patient.

In addition, for extending the liquid transfusing line, it suffices to insert and fit the male connector 323 of one connector 32 into the female connector 322 of the other connector 32, so that it is possible to extend the liquid transfusing line while dosing the transfusion (for example, dosing a tiny amount of a drug) via the liquid transfusing tube already connected. This makes it possible to obviate the risk of the situation where the symptom of the patient might be changed due to a change in the concentration of the drug in the blood, for example.

Besides, in extending the liquid transfusing line, it is unnecessary to open the liquid transfusing line, reassemble the system, and reconnect the components. This makes it possible to obviate the risks of misconnection of the liquid transfusing lines, an increase in the chance of route contamination by bacteria, and the like.

Incidentally, in the present invention, the number of the liquid transfusing tube(s) in the liquid transfusing tube set may be one, or may be three or more.

In addition, in the present invention, in the case where the liquid transfusing tube set includes a plurality of liquid transfusing tubes, the liquid transfusing tubes may all be the same, or may all be different, or some of them may be the same.

Figure 4:
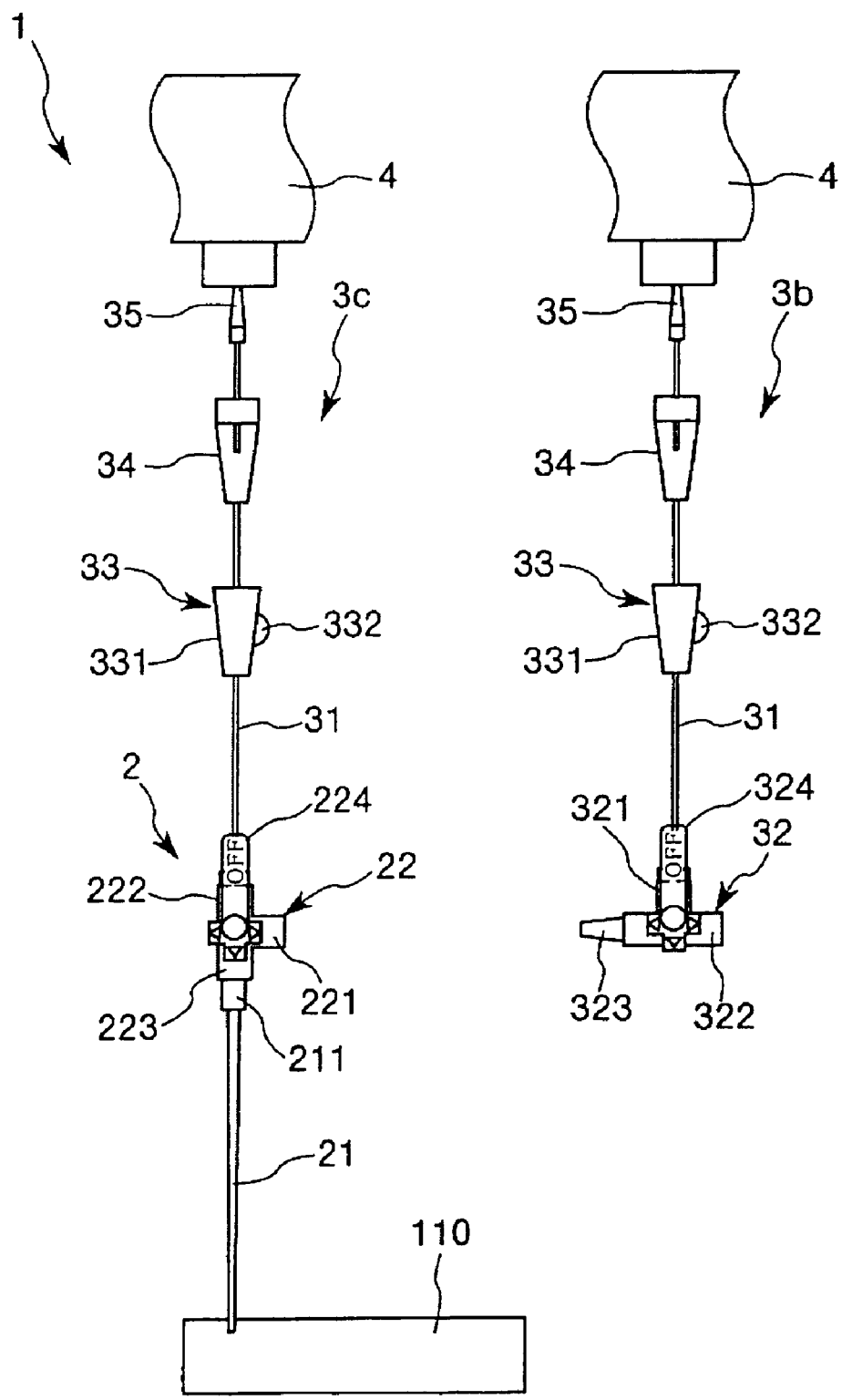
FIG. 4 is a plan view showing a modified example of the first embodiment of the liquid transfusing tube set according to the present invention.

Besides, in the present invention, as shown for example in FIG. 4, the liquid transfusing tube 3a of the liquid transfusing tube set 1 may be replaced by a liquid transfusing tube 3c.

In this liquid transfusing tube set 1, a male connector not shown is provided at one end part (distal end) of the tube 31 of the liquid transfusing tube 3c, and the male connector is connected liquid-tight with a female connector 222 of a liquid dosing part side connector 22. Incidentally, the distal end of the tube 31 may be joined directly to the female connector 222.

Now, another embodiment of the liquid transfusing tube according to the present invention will be described below.

Figure 5:
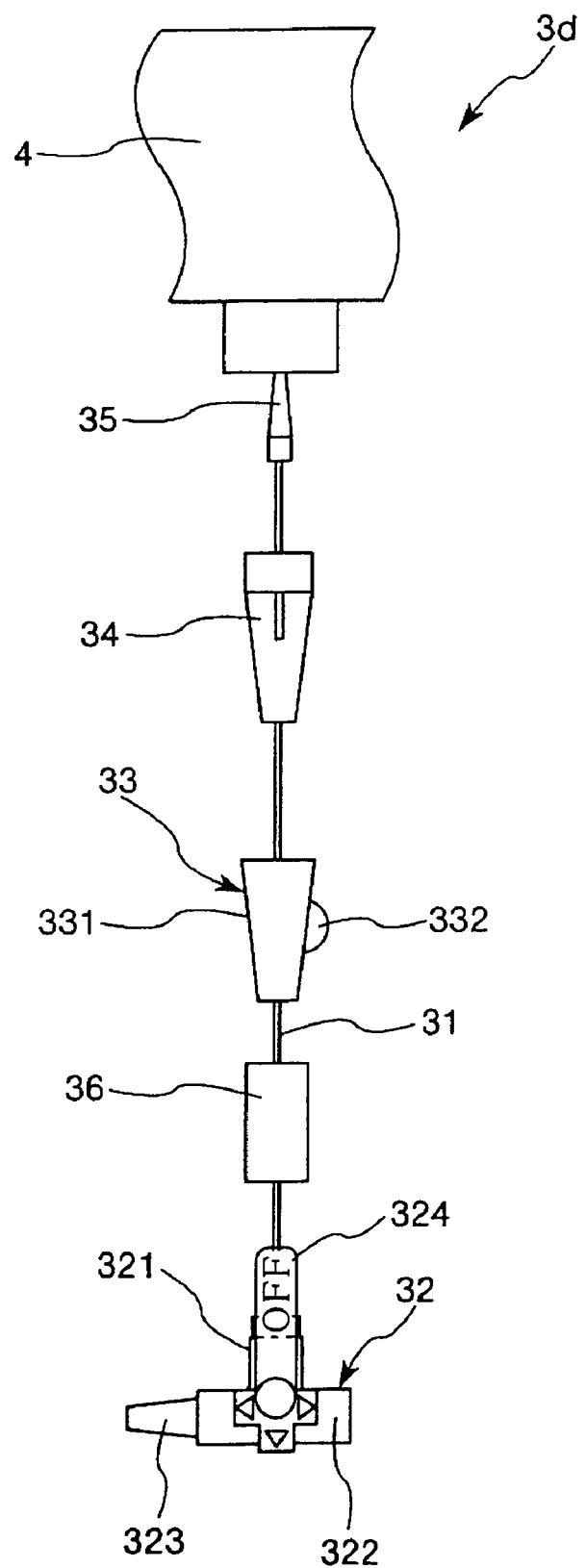
FIG. 5 is a plan view showing another embodiment of the liquid transfusing tube according to the present invention.
Figure 6:
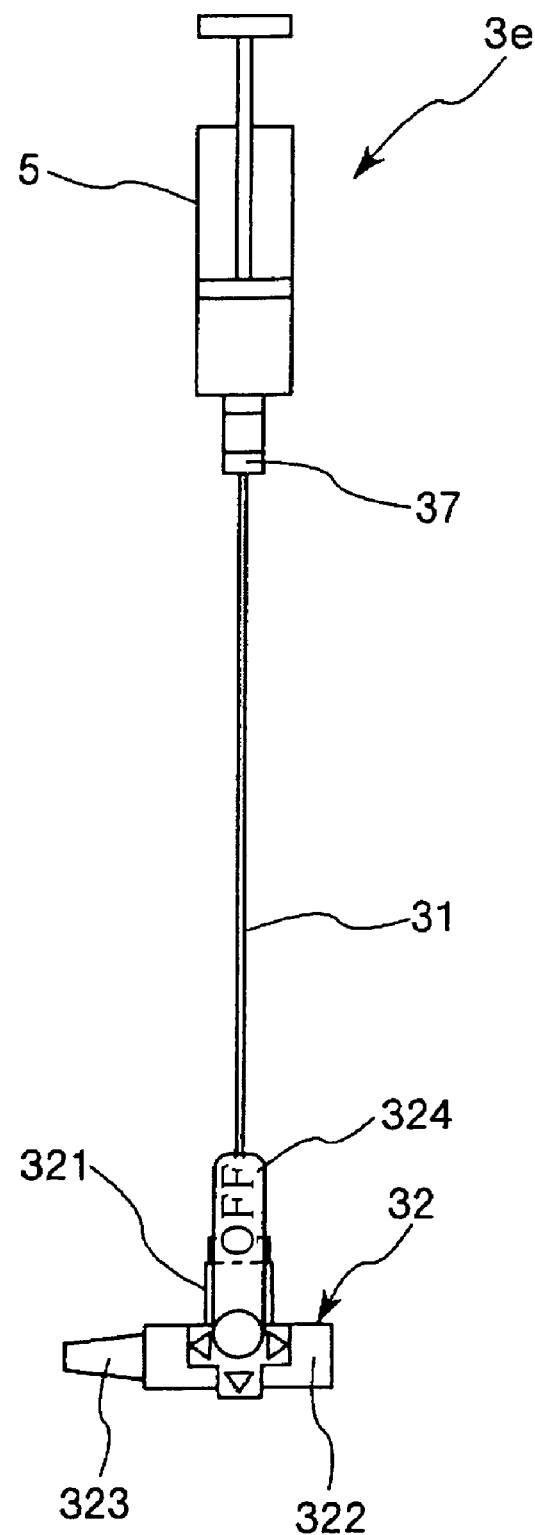
FIG. 6 is a plan view showing a further embodiment of the liquid transfusing tube according to the present invention.

FIGS. 5 and 6 are plan views showing another embodiment of the liquid transfusing tube according to the present invention.

Hereinafter, description will be centered on the differences from the above-described liquid transfusing tubes 3a, 3b, and description of the same points as above will be omitted.

The liquid transfusing tube 3d shown in FIG. 5 includes, at an intermediate part of a tube 31, a check valve 36 as backflow inhibitive means for permitting the flow from a bottle needle (connection part) 35 to a connector 32 and for inhibiting the flow in the reverse direction.

The check valve 36 is preferably disposed between the connector 32 and a roller klemme 33. Further, the check valve 36 is preferably disposed in the vicinity of the connector 32.

Specific examples of the check valve 36 include one that has a valve main body provided therein with a pair of plate-like opening/closing members. The opening/closing members are in close contact with each other on the distal end side by elastic forces (recovering forces) and are so tapered as to be spaced farther apart toward the proximal end side. Therefore, in normal condition, the channel in the check valve 36 is closed. In the case where the transfusion flow is directed from the distal end side toward the proximal end side, the liquid exerts a pressure on the outside surfaces of the opening/closing members, acting to urge the opening/closing members into close contact with each other. Therefore, the transfusion would not flow from the distal end side toward the proximal end side.

On the other hand, in the case where the transfusion flow is directed from the proximal end side toward the distal end side, the liquid exerts a predetermined pressure on the inside surfaces (taper surfaces) of the opening/closing members, so that the opening/closing members are deformed by the pressure so as to be spaced apart from each other, and the channel in the check valve 36 is opened. As a result, the transfusion flows from the proximal end side toward the distal end side.

According to this liquid transfusing tube 3d, even where the connector 32 does not have a channel changeover function, the check valve 36 can prevent the transfusion from flowing to the upstream side (proximal end side) of the liquid transfusing tube 3d, even when another liquid transfusing tube (for example, a liquid transfusing tube 3e which will be described later) is connected to the connector 32 of the liquid transfusing tube 3d and the transfusion is dosed from the another liquid transfusing tube under a certain pressure; thus, the transfusion can be securely dosed into the patient.

In addition, according to the liquid transfusing tube 3d, the same effects as those of the above-described liquid transfusing tubes 3a, 3b can be obtained.

The liquid transfusing tube 3e shown in FIG. 6 includes, at the proximal end of a tube 31, a female connector 37, which is connected to the distal end (mouth part) of a syringe (containing part) 5 containing a transfusion, as a connection part for connection with the syringe 5.

Besides, for example, a tiny amount regulation orifice or the like may be provided at an intermediate part of the tube 31, as flow rate regulation means for regulating the flow rate of the transfusion.

According to the liquid transfusing tube 3e, the same effects as those of the above-mentioned liquid transfusing tubes 3a, 3b can be obtained.

In addition, the liquid transfusing tube 3e may include, at an intermediate part of the tube 31, a check valve 36 as backflow inhibitive means for permitting the flow from a connector (connection part) 37 toward the connector 32 and inhibiting the flow in the reverse direction.

The check valve 36 is preferably disposed in the vicinity of the connector 32.

Incidentally, the structure and the functions of the check valve 36 are the same as those of the check valve 36 of the above-described liquid transfusing tube 3d shown in FIG. 5, so that the description thereof is omitted.

Due to the presence of the check valve 36, even where the connector 32 does not have a channel changeover function, the check valve 36 can prevent the transfusion from flowing to the upstream side (proximal end side) of the liquid transfusing tube 3e, even when another liquid transfusing tube is connected to the connector 32 of the liquid transfusing tube 3e and the transfusion is dosed from the another liquid transfusing tube under a certain pressure; thus, the transfusion can be securely dosed into the patient.

The above-mentioned liquid transfusing tubes 3a, 3b, 3d, and 3e can be used either singly or in combination of two or more of them, in the above-described liquid transfusing tube set 1.

Now, a second embodiment of the liquid transfusing tube set according to the present invention will be described below.

Figure 7:
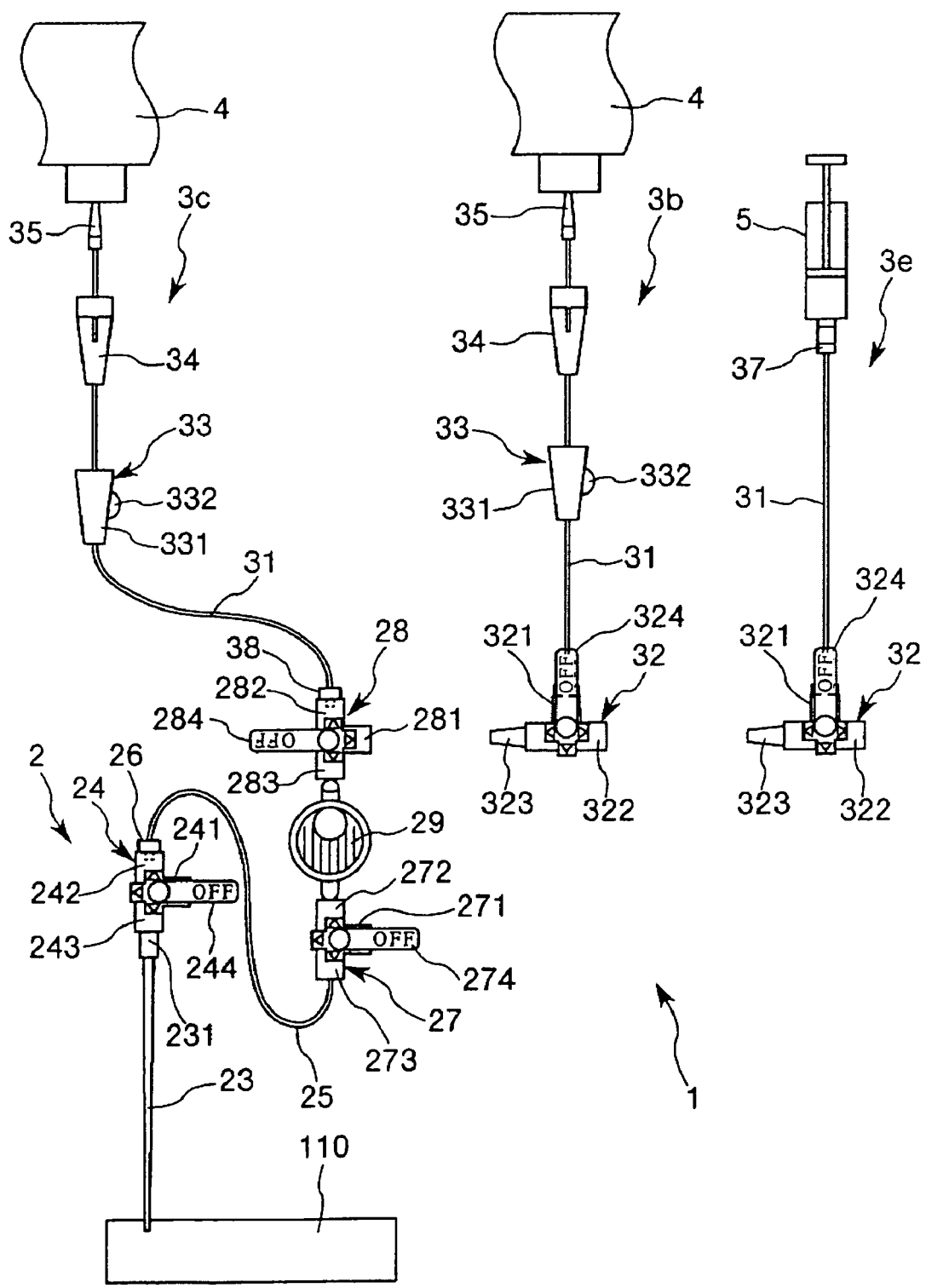
FIG. 7 is a plan view showing a second embodiment of the liquid transfusing tube set according to the present invention.
Figure 8:
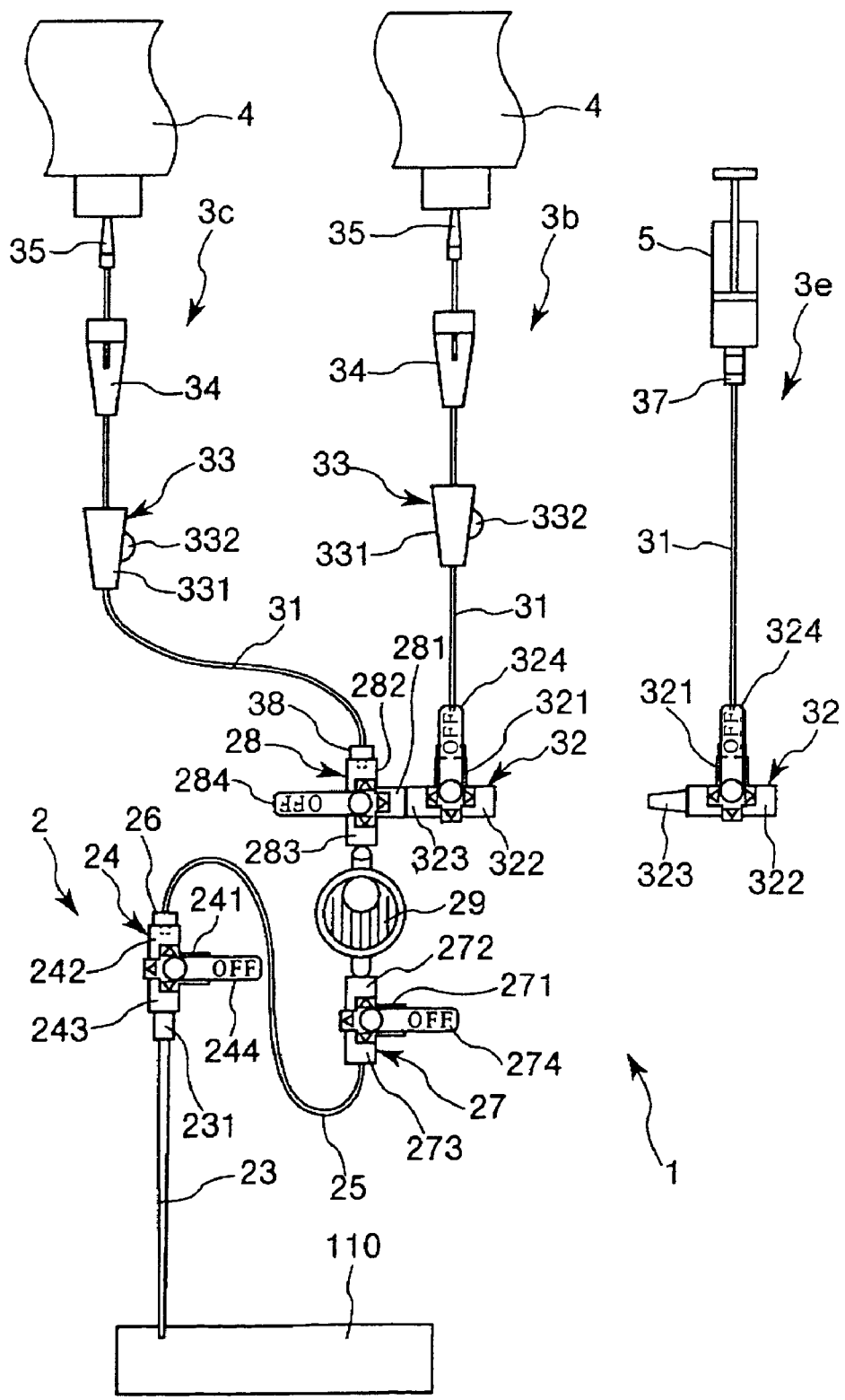
FIG. 8 is a plan view showing the condition where one of liquid transfusing tubes of the liquid transfusing tube set shown in FIG. 7 is connected.
Figure 9:
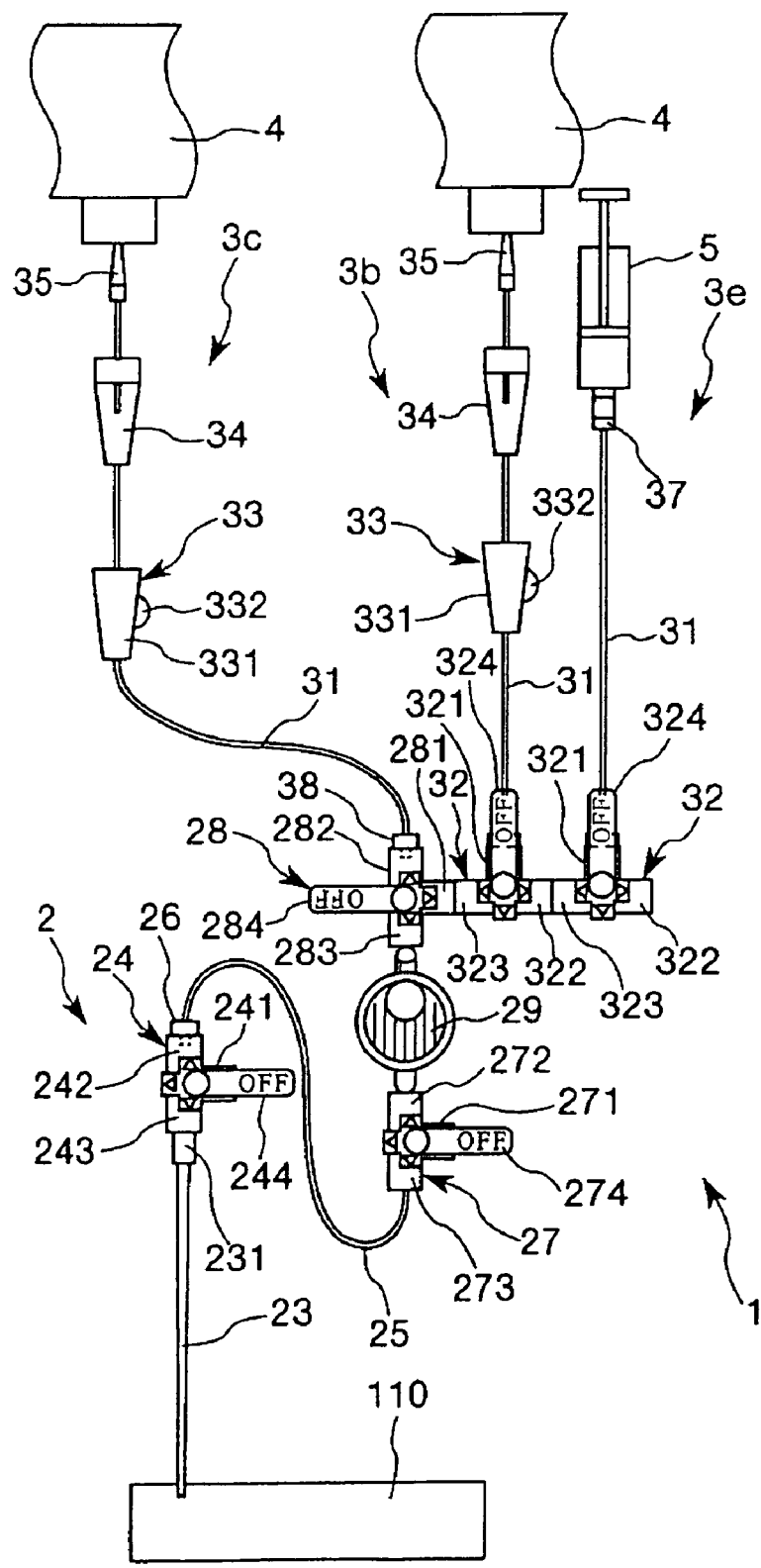
FIG. 9 is a plan view showing the condition where each of the liquid transfusing tubes of the liquid transfusing tube set shown in FIG. 7 is connected.

FIG. 7 is a plan view showing the second embodiment of the liquid transfusing tube set according to the present invention, FIG. 8 is a plan view showing the condition where one of liquid transfusing tubes of the liquid transfusing tube set shown in FIG. 7 is connected, and FIG. 9 is a plan view showing the condition where each of the liquid transfusing tubes of the liquid transfusing tube set shown in FIG. 7 is connected.

Hereinafter, description will be centered on the differences of the liquid transfusing tube set 1 in the second embodiment from the above-described first embodiment, and description of the same points as above will be omitted.

The liquid transfusing tube set 1 in the second embodiment shown in these figures is the same as the above-described first embodiment, except that a liquid dosing part 2 is different from the above.

As shown in FIG. 7, the liquid transfusing tube set 1 according to the second embodiment includes the liquid dosing part 2, and the same liquid transfusing tubes 3b, 3c, and 3e in the first embodiment described above.

The liquid dosing part 2 includes an indwelling needle or catheter (in this embodiment, a catheter 23) left indwelling in a blood vessel 110 of a patient, a connector (in this embodiment, a three-way cock) 24 connected to the proximal end of the indwelling needle or catheter (in this embodiment, the catheter 23), a tube 25 which is flexible and constitutes a liquid transfusing channel, a male connector 26 provided at the distal end of the tube 25, a connector (in this embodiment, a three-way cock) 27 provided at the proximal end of the tube 25, a liquid dosing part side connector (in this embodiment, a three-way cock) 28, and a bacteria-removing filter 29.

Incidentally, the indwelling needle or catheter and the connector 24 may be connected to each other through a tube.

The connector 24 includes two female connectors 241, 242, a male connector 243, and an operating lever (operating part) 244, and the communication pattern among the inner cavity of the female connector 241, the inner cavity of the female connector 242, and the inner cavity of the male connector 243 can be selected by means of the operating lever 244 (thus, the connector 24 has a channel changeover function for changing over the channel).

The catheter 23 has an outlet port 231 at its proximal end, and the male connector 243 of the connector 24 is in liquid-tight connection with the outlet port 231.

In addition, the male connector 26 provided at the distal end of the tube 25 is in liquid-tight connection with the female connector 241 of the connector 24.

The liquid dosing part side connector 28 includes three female connectors 281, 282, 283, and an operating lever (operating part) 284, and is so configured that the communication pattern among the inner cavity of the female connector 281, the inner cavity of the female connector 282, and the inner cavity of the female connector 283 can be selected by means of the operating lever 284 (thus, the liquid dosing part side connector 28 has a channel changeover function for changing over the channel).

Similarly, the connector 27 includes three female connectors 271, 272, 273, and an operating lever (operating part) 274, and is so configured that the communication pattern among the inner cavity of the female connector 271, the inner cavity of the female connector 272, and the inner cavity of the female connector 273 can be selected by means of the operating lever 274 (thus, the connector 27 has a channel changeover function for changing over the channel).

Incidentally, details of the connectors 24, 27 and the liquid dosing part side connector 28 are substantially the same as those of the liquid dosing part side connector 22 in the first embodiment described above. Therefore, the description thereof is omitted.

As shown in FIG. 7, a male connector 38 is provided at the distal end of a tube 31 of the liquid transfusing tube 3c, and the male connector 38 is in liquid-tight connection with the female connector 282 of the liquid dosing part side connector 28.

In addition, the bacteria-removing filter 29 is provided on the downstream side relative to the liquid dosing part side connector 28, and the connector 27 is provided on the downstream side of the filter 29.

Specifically, one end side (downstream side) of the filter 29 is connected liquid-tight to the female connector 272 of the connector 27, and the other end side (upstream side) of the filter 29 is connected liquid-tight to the female connector 283 of the liquid dosing part side connector 28.

The female connector 271 of the connector 27 constitutes a mixing injection port to which the liquid transfusing tube 3b or 3e or the like is connected.

In dosing a transfusion into a patient, the male connector 323 of the connector 32 of the liquid transfusing tube 3b or 3e is connected to the female connector 281 of the liquid dosing part side connector 28 or to the female connector 322 of a connector 32 of an other liquid transfusing tube (3b in FIG. 8) connected to the liquid dosing part side connector 28 in the case where the transfusion may or must be passed through the filter 29. In the case where the transfusion must not be passed through the filter 29, the male connector 323 is connected to the male connector 271 of the connector 27 or to the female connector 322 of the connector 32 of the other liquid transfusing tube connected to the connector 27.

Incidentally, while the male connector 323 of the connector 32 of the liquid transfusing tube 3b or 3e or the like, for example, is connected to the connector 27 in this embodiment, there may be adopted a configuration in which, for example, the female connector 322 of the connector 32 of the liquid transfusing tube 3b or 3e is connected to the connector 27, or a configuration in which both the male connector 323 and the female connector 322 of the connector 32 of the liquid transfusing tube 3b or 3e can be connected to the connector 27.

In the case where the female connector 322 of the connector 32 of the liquid transfusing tube 3b or 3e is connected to the connector 27, for example, the female connector 271 of the connector 27 is replaced by a male connector, which is so shaped as to be capable of liquid-tight connection with the female connector 322 of the connector 32 of the liquid transfusing tube 3b or 3e.

Now, the functions of (method of using) the liquid transfusing tube set 1 will be described below.

Here, description will be made by taking as an example the case where the liquid transfusing tube 3c is used as a first liquid transfusing line (first liquid transfusing route) for dosing a transfusion into a patient, i.e., principally a liquid transfusing tube for flow therethrough of a high-calorie transfusion, a fundamental liquid, or the like, while the liquid transfusing tube 3b is used as a second liquid transfusing line (second liquid transfusing route) for dosing a transfusion into the patient, i.e., principally as an auxiliary route, for example, a liquid transfusing tube for flow therethrough of a lipid emulsion, a remedy, an antibiotic drug, or the like, and the liquid transfusing tube 3e is used as a third liquid transfusing line (third liquid transfusing route) for dosing a transfusion into the patient, i.e., principally as an auxiliary route, for example, as a liquid transfusing tube for flow therethrough of a tiny quantity of a remedy or the like.

In connecting the liquid transfusing tube 3c, first, a high calorie transfusion, for example, is prepared in a liquid transfusing bag 4.

Next, as shown in FIG. 7, a bottle needle 35 of the liquid transfusing tube 3c is made to pierce (puncture) a plug (rubber plug) of the liquid transfusing bag 4 in which the transfusion is contained. This ensures that the liquid transfusing bag 4 and the liquid transfusing tube 3c are connected to each other through the bottle needle 35, resulting in the condition where the transfusion can be supplied from the liquid transfusing bag 4 to the side of the liquid transfusing tube 3c.

Subsequently, priming of the channel of the liquid transfusing tube 3c is performed.

Next, the male connector 38 of the liquid transfusing tube 3c is inserted and fitted into the female connector 282 of the liquid dosing part side connector 28 on the side of the catheter 23 left indwelling in a blood vessel (for example, a central vein or the like) 110 of a patient. This makes liquid-tight connection between the female connector 282 of the liquid dosing part side connector 28 and the male connector 38 of the liquid transfusing tube 3c.

Subsequently, an operating lever 284 of the liquid dosing part side connector 28 is moved to the position of the female connector 281, whereas an operating lever 274 of the connector 27 is moved to the position of the female connector 271, and an operating lever 244 of the connector 24 is moved to the position of the female connector 241. This results in that the inner cavity of the female connector 282 and the inner cavity of the female connector 283 in the liquid dosing part side connector 28 are communicated with each other, whereas the inner cavity of the female connector 272 and the inner cavity of the female connector 273 in the connector 27 are communicated with each other, and the inner cavity of the female connector 242 and the inner cavity of the male connector 243 in the connector 24 are communicated with each other.

This makes it possible to dose the high-calorie transfusion into the patient via the filter 29.

Next, a roller klemme 33 of the liquid transfusing tube 3c is operated so as to regulate the flow rate (dose rate) of the transfusion in the liquid transfusing tube 3c to a prescribed flow rate (prescribed dose rate) of the high-calorie transfusion, and the liquid is dosed.

Subsequently, in connecting a liquid transfusing tube 3b used for dosing, for example, an antibiotic drug, a physiological saline containing the antibiotic drug dissolved therein is first prepared in the liquid transfusing bag 4.

Next, as shown in FIG. 7, a bottle needle 35 of the liquid transfusing tube 3b is made to pierce (puncture) a plug (rubber plug) of the liquid transfusing bag 4 in which the transfusion is contained. This ensures that the liquid transfusing bag 4 and the liquid transfusing tube 3b are connected to each other through the bottle needle 35, resulting in the condition where the transfusion can be supplied from the liquid transfusing bag 4 to the side of the liquid transfusing tube 3b.

Subsequently, priming of the channel of the liquid transfusing tube 3b is carried out.

Next, as shown in FIG. 8, the male connector 323 of the connector 32 of the liquid transfusing tube 3b is inserted and fitted into the female connector 281 of the liquid dosing part side connector 28. This makes liquid-tight connection between the female connector 281 of the liquid dosing part side connector 28 and the male connector 323 of the connector 32 of the liquid transfusing tube 3b.

Subsequently, the operating lever 324 of the connector 32 of the liquid transfusing tube 3b is moved to the position of the female connector 322, and the operating lever 284 of the liquid dosing part side connector 28 is moved to the position where no connector is present. This results in that the inner cavity of the female connector 321 and the inner cavity of the male connector 323 in the connector 32 of the liquid transfusing tube 3b are communicated with each other, and the inner cavity of the female connector 281, the inner cavity of the female connector 282, and the inner cavity of the female connector 283 in the liquid dosing part side connector 28 are all communicated with one another.

This makes it possible to dose an antibiotic drug into the patient through the filter 29.

Next, the roller klemme 33 of the liquid transfusing tube 3b is operated to regulate the flow rate (dose rate) of the transfusion in the liquid transfusing tube 3b to a prescribed flow rate (prescribed dose rate) of the antibiotic drug, thereby dosing the transfusion.

Subsequently, in connecting the liquid transfusing tube 3e used for dosing, for example, nitroglycerine at regular time intervals depending on the condition of the patient, first, nitroglycerine is sucked and contained into a syringe 5 as shown in FIG. 8.

Next, the female connector 37 is inserted and fitted into the distal end (mouth part) of the syringe 5. This makes liquid-tight connection between the distal end of the syringe 5 and the female connector 37, resulting in the condition where the transfusion can be supplied from the syringe 5 to the side of the liquid transfusing tube 3e.

Subsequently, the syringe 5 is set to a syringe pump which is not shown.

Next, priming of the channel of the liquid transfusing tube 3e is performed.

Subsequently, as shown in FIG. 9, the male connector 323 of the connector 32 of the liquid transfusing tube 3e is inserted and fitted into the female connector 322 of the connector 32 of the liquid transfusing tube 3b. This makes liquid-tight connection between the female connector 322 of the connector 32 of the liquid transfusing tube 3b and the male connector 323 of the connector 32 of the liquid transfusing tube 3e.

Next, the operating lever 324 of the connector 32 of the liquid transfusing tube 3e is moved to the position of the female connector 322. This results in that the inner cavity of the female connector 321 and the inner cavity of the male connector 323 in the connector 32 of the liquid transfusing tube 3e are communicated with each other.

Subsequently, the operating lever 324 of the connector 32 of the liquid transfusing tube 3b is moved to the position where no connector is present. This results in that the inner cavity of the female connector 321, the inner cavity of the female connector 322, and the inner cavity of the male connector 323 in the connector 32 of the liquid transfusing tube 3b are all communicated with one another.

As a result, nitroglycerine can be dosed into the patient through the filter 29.

Next, the operating part on the syringe pump side is operated to regulate the flow rate (dose rate) of the transfusion in the liquid transfusing tube 3e to a prescribed flow rate (prescribed dose rate) of nitroglycerine, and the transfusion is dosed.

In this manner it is possible to dose (mixingly inject) the patient with the high-calorie transfusion via the liquid transfusing tube 3c, with the physiological saline containing an antibiotic drug dissolved therein via the liquid transfusing tube 3b, and with nitroglycerine via the liquid transfusing tube 3e.

According to this liquid transfusing tube set 1, the same effects as in the first embodiment described above can be obtained.

While the liquid transfusing tube and the liquid transfusing tube set according to the present invention have been described above based on the embodiments shown in the figures, the invention is not limited to the embodiments, and the configurations of the individual parts can be replaced by arbitrary configurations having the same or equivalent functions.

Incidentally, the present invention may be carried out by combining arbitrary two or more configurations (characteristic features) of the above-described embodiments.

In addition, the liquid transfusing tube set according to the present invention may lack a part of the liquid dosing part, for example, the indwelling needle or catheter or the like. It suffices for the liquid dosing part to have the liquid dosing part side connector (for example, the liquid dosing part may be constituted only of the liquid dosing part side connector).

INDUSTRIAL APPLICABILITY

As has been described above, according to the present invention, the liquid transfusing line (liquid transfusing route) can be extended readily, quickly, and assuredly.

The invention claimed is:

1. A liquid transfusing tube set comprising:
at least one liquid transfusing tube comprising:
a tube constituting a liquid transfusing channel and having an axis;
a connector provided at one end of said tube; and
a connection part provided on an opposite end of said tube and connected to a side of a containing part containing a transfusion; wherein
said connector includes a male connector and a female connector, the axis of said male connector and the axis of said female connector substantially coincide with each other, and the axis of said tube is substantially orthogonal to the axis of the male connector and the axis of said female connector;
a liquid dosing part for dosing a patient with said transfusion, said liquid dosing part having a liquid dosing part side connector connectable to one of said male connector and said female connector of said connector of said liquid transfusing tube; and
in a condition where one of said male connector and said female connector of said connector of said liquid transfusing tube and said liquid dosing part side connector of said liquid dosing part are connected with each other, the other of said male connector and said female connector of said connector of said liquid transfusing tube is connectable to another liquid transfusing tube other than said liquid transfusing tube; and the other of said male connector and said female connector of said connector of said liquid transfusing tube is exposed as an open connection port to receive a male or female connector of the another liquid transfusing tube.

2. The liquid transfusing tube set as set forth in claim 1, wherein said connector has a channel changeover function for changing over the channel.

3. The liquid transfusing tube set as set forth in claim 1, wherein said connector is so configured that a communication pattern among an inner cavity of said tube, an inner cavity of said male connector, and an inner cavity of said female connector can be selected.

4. The liquid transfusing tube set as set forth in claim 1, wherein said liquid dosing part has a bacteria-removing filter.

5. The liquid transfusing tube set as set forth in claim 4, wherein said bacteria-removing filter is provided on the downstream side relative to said liquid dosing part side connector.

6. The liquid transfusing tube set as set forth in claim 4, wherein said liquid dosing part has a mixing injection port on the downstream side of said bacteria-removing filter.

7. The liquid transfusing tube set as set forth in claim 1, wherein one end of a the another liquid transfusing tube has a connection part connected to another liquid container, and an opposing end of said another liquid transfusing tube is connected to said liquid dosing part side connector.

8. The liquid transfusing tube set as set forth in claim 1, wherein said liquid dosing part side connector is branched into a plurality of parts so that a connector provided on one end of the another liquid transfusing tube and said connector of said liquid transfusing tube can be simultaneously connected, an opposing end of the another liquid transfusing tube having a connection part connected to another containing part other than said containing part associated with said liquid transfusing tube.

9. The liquid transfusing tube set as set forth in claim 1, wherein the connector is directly connected to said tube.

10. The liquid transfusing tube set as set forth in claim 1, wherein the male connector and the female connector are on opposing sides of said connector.

* * * * *